United States Patent [19]

Samejima et al.

[11] 4,332,733

[45] Jun. 1, 1982

[54] PROCESS FOR LIQUEFYING ACID ANHYDRIDE

[75] Inventors: Hiroshi Samejima; Mareki Miura; Yoshinobu Onuma, all of Ibaraki, Japan

[73] Assignee: Mitsubishi Petrochemical Co., Ltd., Tokyo, Japan

[21] Appl. No.: 224,570

[22] PCT Filed: Feb. 28, 1979

[86] PCT No.: PCT/JP79/00049

§ 371 Date: Oct. 28, 1980

§ 102(e) Date: Oct. 28, 1980

[87] PCT Pub. No.: WO80/01804

PCT Pub. Date: Sep. 4, 1980

[51] Int. Cl.[3] .......... C07D 307/89

[52] U.S. Cl. .......... 549/240; 549/255

[58] Field of Search .......... 260/346.6

[56] References Cited

U.S. PATENT DOCUMENTS

| | | | |
|---|---|---|---|
| 3,873,501 | 3/1975 | Saga | 260/47 EA |
| 3,927,038 | 12/1975 | Liakumovich et al. | 260/346.6 X |
| 4,198,340 | 4/1980 | Ariga et al. | 260/346.3 |

FOREIGN PATENT DOCUMENTS

| | | |
|---|---|---|
| 50-14280 | 5/1975 | Japan . |
| 50-27517 | 9/1975 | Japan . |
| 52-5495 | 2/1977 | Japan . |
| 53-130638 | 11/1978 | Japan . |
| 906017 | 9/1962 | United Kingdom . |

OTHER PUBLICATIONS

Craig, JACS, vol. 72, (1950), pp. 1678–1681.

*Primary Examiner*—Richard Raymond
*Attorney, Agent, or Firm*—Sughrue, Mion, Zinn, Macpeak and Seas

[57] ABSTRACT

A normally solid Diels-Alder reaction product between maleic anhydride and decatriene can be liquefied by heat-treating at from 60° to 250° C. for from 10 minutes to 10 hours in the presence of a compound selected from the following groups (a) to (e):

(a) alkali metal salts;
(b) nitrogen atom-containing organic compounds;
(c) phosphorus atom-containing compounds selected from phosphines and quaternary phosphonium salts;
(d) thiocyanates; and
(e) solid basic compounds.

14 Claims, No Drawings

PROCESS FOR LIQUEFYING ACID ANHYDRIDE

FIELD OF THE INVENTION

This invention relates to a process for liquefying a product of Diels-Alder reaction between maleic anhydride and decatriene, which is in a solid state at normal temperatures.

The resulting liquid acid anhydride is useful as a curing agent for epoxy resin and as a starting material for unsaturated alkyd. Hereinafter, the curing agent is referred to as a "hardener."

BACKGROUND OF THE INVENTION

Diels-Alder reaction products between decatriene and maleic anhydride (hereinafter referred to as "maleinized decatriene") such as a reaction product between maleic anhydride and allo-ocimene (hereinafter referred to as "maleinized allo-ocimeme") and a reaction product between maleic anhydride and myrcene (hereinafter referred to as "maleinized myrcene") can be used as hardeners for epoxy resins and as acid components for preparing unsaturated alkyd resin. However, many of these maleinized decatrienes are in a solid state at room temperatures and, from the point of view of reactivity and workability, it is desirable to liquefy them for the application to the above-described uses. Thus, liquefaction of the solid maleinized decatriene is necessary.

As the conventional process for liquefying maleinized allo-ocimene, B.P No. 906,017, for example, describes to liquefy maleinized allo-ocimene by heat-treating at temperatures of from 190° to 240° C. for a long time to cause thermal isomerization. However, such process of isomerization by heat-treating for a long time involves thermal decomposition even when conducted in a nitrogen stream, and hence it has the defect that liquefied, maleinized allo-ocimene is obtained only in a low yield after purification by distillation. And, the liquefied product obtained by the distillation purification often forms crystals 2 to 3 days after the preparation though it is temporarily liquid upon preparation and, even when it is in a liquid state at normal temperatures, it crystallizes at low temperatures of about 0° to 10° C. This specification describes, in Example 6, that maleinized allo-ocimene heat-treated at 210° to 220° C. for 14 hours crystallizes when allowed to stand, and that additional heat treatment for 5 hours at 210° to 220° C. provides a liquid product which does not crystallize even when allowed to stand at normal temperatures. However, such process capable of liquefying maleinized allo-ocimene only through long-time heat treatment is seriously disadvantageous from the point of industrial practice.

U.S. Pat. No. 3,078,235 describes a liquid epoxy resin hardener prepared by blending maleinized allo-ocimene, maleinized myrcene, and hexahydrophthalic anhydride. However, blending of the normally solid materials to liquefy them requires a melt-mixing step, thus leading to high cost.

The present invention provides a process for liquefying normally solid maleinized decatriene with ease and with industrial advantages.

DISCLOSURE OF THE INVENTION

This invention provides a process of liquefying normally solid maleinized decatriene by heat-treating it in the presence of a compound selected from the following groups (a) to (e):

(a) alkali metal salts;

(b) nitrogen-containing organic compounds;

(c) phosphorus-containing compounds selected from phosphines and quaternary phosphonium salts;

(d) thiocyanates; and (e) solid basic compounds (except the alkali metal salts belonging to group (a) described above).

Furthermore, the present invention provides a process for liquefying maleinized decatriene which is in a solid state at room temperatures by previously heat-treating it in the presence of a compound selected from the above-described groups (a) to (e), and heat-treating the previously heat-treated product in the presence of an acidic catalyst or a noble metal catalyst.

As is stated above, normally solid maleinized decatriene can easily be liquefied by heat-treating in the presence of a compound selected from the above-described groups (a) to (e).

This liquefaction may be attributed to the formation of several isomers due to isomerization of maleinized decatriene, thus copresence of these several isomers causing reduction of solidifying point. However, details of the mechanism still involve many ambiguous points. For example, with respect to heat treatment of maleinized allo-ocimene as the maleinized decatriene in the presence of sodium iodide, the liquefaction mechanism is believed to be as follows.

Commercially available allo-ocimene contains two isomers of trans-cis isomer and trans-trans isomer: content of the former being from 50 to 70%; and content of the latter being from 30 to 50%.

Such allo-ocimene can be easily converted to maleinized allo-ocimene by adding maleic anhydride according to Diels-Alder reaction. Maleinized allo-ocimene thus obtained is usually an isomer mixture composed of the following two isomers (I) and (II) and has a melting point of 70° C. or above, for example, 83° to 84° C., thus being of course in a solid state at room temperatures (20° to 30° C.).

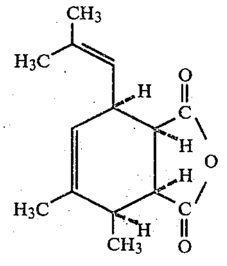

(I)

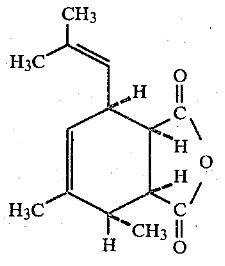

(II)

When heat-treating this normally solid maleinized allo-ocimene in the presence of sodium iodide, isomers of the following formulae (III) and (IV), etc. are produced from part of the above-described isomers (I) and (II) and, in addition, isomerization reaction of double bond takes place. Thus, the heat-treated product contains extremely many kinds of isomers, and the copresence of such isomers is considered to reduce solidifying point and liquefy the product.

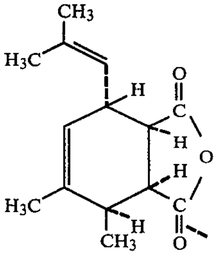

(III)

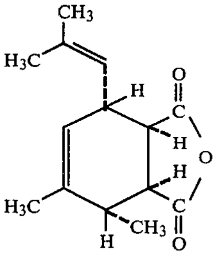

(IV)

The thus obtained maleinized decatriene which is in a liquid state at normal temperatures facilitates admixing thereof with an epoxy resin due to the liquid properties, thus being optimal as a hardener for epoxy resins.

PREFERRED EMBODIMENT OF THE INVENTION

This invention will be described in more detail below.

(1) Maleinized decatrienes

As the normally solid maleinized decatrienes to be used in the process of the present invention, there are illustrated normally solid maleinized decatrienes obtained by subjecting the following decatrienes to Diels-Alder reaction with maleic anhydride.

(i) Alo-ocimene

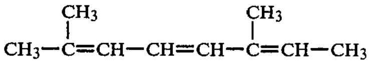

(ii) Ocimene

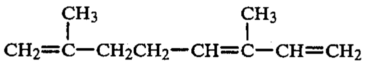

(iii) 2,7-Dimethyl-1,3,7-octatriene

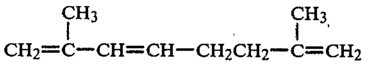

(iv) 2,6-Dimethyl-1,3,6-octatriene

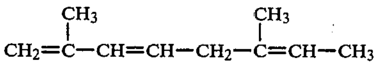

Particularly preferable maleinized decatrienes in the present invention are a Diels-Alder reaction product between allo-ocimene or 2,6-dimethyl-1,3,6-octatriene and maleic anhydride, or maleinized allo-ocimene, and a Diels-Alder reaction product between a mixture of allo-ocimene and myrcene or α-pinene and maleic anhydride.

(2) Isomerization Catalyst

Compounds of groups (a) to (e) to be allowed to exist upon liquefaction of solid maleinized decatriene according to the process of the present invention (hereinafter referred to as "isomerization catalysts") will be described in detail below.

(a) Alkali Metal Salts

The exemplary alkali metal salts include, for example, alkali metal halides such as lithium chloride, lithium bromide, sodium chloride, sodium bromide, potassium chloride, potassium bromide, rubidium chloride, cesium chloride, lithium iodide, sodium iodide, potassium iodide, rubidium iodide, cesium iodide, rubidium bromide, cesium bromide, etc.; alkali metal inorganic acid salts such as lithium sulfate, lithium nitrate, lithium nitrite, lithium phosphate, lithium cyanide, lithium carbonate, sodium sulfate, sodium nitrate, sodium phosphate, sodium cyanide, sodium carbonate, potassium sulfate, potassium nitrate, potassium phosphate, potassium cyanide, potassium carbonate, etc.; alkali metal organic acid salts such as lithium acetate, lithium benzoate, lithium octanoate, lithium stearate, lithium salicylate, lithium oxalate, sodium acetate, sodium oleate, sodium benzoate, potassium acetate, potassium oleate, potassium lactate, etc.; alkali metal salts of phenols such as lithium phenolate, lithium resorcinolate, bisphenol A lithium salt, sodium phenolate, potassium phenolate, etc.; alkali metal salts of alcohols such as sodium methylate, lithium methylate, sodium ethylate, potassium ethylate, etc.; and the like.

Of these, sodium iodide, potassium iodide, lithium bromide, potassium bromide, and sodium bromide are preferable due to their easy availability and inexpensiveness.

(b) Nitrogen-containing Organic Compounds

Nitrogen-containing organic compounds that can be used in the present invention as isomerization catalysts include various nitrogen-containing organic compounds including organic compounds having a primary, secondary, tertiary amine-type and/or quaternary ammonium-type nitrogen atom or atoms, salts of these compounds, and like derivatives.

Typical examples of the primary amine-type nitrogen atom-containing organic compounds are as follows.

(i) Alkylamines:

For example, there are oleylamine, stearylamine, 2-ethylhexylamine, etc.

(ii) Amines represented by the following general formula:

$$H_2N(CH_2)_nNH_2 (n=1 \text{ to } 20)$$

For example, there are ethylenediamine, propylenediamine, hexamethylenediamine, etc.

(iii) Polyalkylenepolyamines represented by the following general formula:

$$H_2N(CH_2)_nNH(CH_2)_nNH_2 (n=2 \text{ to } 8)$$

For example, there are propylenetriamine, butylenetriamine, diethylenetriamine, etc.

(iv) Polyethylenepolyamines represented by the following general formula:

$$H_2N[(CH_2)_2NH]_n(CH_2)_2NH_2 (n=2 \text{ to } 10)$$

For example, there are triethylenetetramine, tetraethylenepentamine, pentaethylenehexamine, etc.

(v) Alkanolamines:

For example, there are aminoethanolamine, ethanolamine, etc.

(vi) Alicyclic amines:

For example, there are menthanediamine, diaminocyclohexane, isophoronediamine, etc.

(vii) Aromatic amines:

For example, there are xylenediamine, tetrachloro-p-xylenediamine, m-phenylenediamine, methylenedianiline, diaminodiphenylsulfone, aniline, toluidine, etc.

Typical examples of the secondary amine-type nitrogen atom-containing organic compounds include, for example, N-methylpiperazine, hydroxyethylpiperazine, piperidine, pyrrolidine, morpholine, diethanolamine, etc.

Typical examples of the tertiary amine-type nitrogen atom-containing organic compounds are as follows.

(i) Aliphatic tertiary diamines:

tertiary amines represented by the following general formula:

$(CH_3)_2N(CH_2)_nN(CH_3)_2$(n=2 to 20)

such as N,N,N',N'-tetramethyl-1,3-butanediamine;

tetramethylguanidine;

tertiary amines represented by the following general formula:

$N[(CH_2)_nCH_3]_3$(n=0 to 20)

such as tri-n-butylamine, tri-2-ethylhexylamine, triamylamine, etc.;

triethanolamine;

2-dimethylamino-2-hydroxypropane;

dialkylaminoethanols represented by the following general formula:

$[CH_3(CH_2)_n]_2N(CH_2)_2OH$(n=1 to 20)

such as dimethylaminoethanolamine, dibutylaminoethanolamine, etc.; and hexamethylphosphoramide.

(ii) Alicyclic tertiary amines:

Examples of the alicyclic tertiary amines include N,N'-dimethylpiperazine, N,N'-bis[(2-hydroxy)propyl]-piperazine, N-alkylmorpholine, 1,4-diazabicyclo[2,2,2]-octane(triethylenediamine), hexamethylenetetramine, N,N-dimethylcyclohexylamine, N-alkylpiperidine, N-methyldicyclohexylamine, N-alkylpyrrolidine, etc.

(iii) Unsaturated cyclic tertiary amines:

Examples of these amines are as follows:

1-hydroxyethyl-2-heptadecylgloxysaridine;

pyridine and the derivative thereof, such as pyridine, α-picoline, β-picoline, γ-picoline, 3,5-lutidine, etc.;

piperazine and the derivatives thereof;

quinoline and the derivatives thereof;

diazabicycloalkenes represented by the following general formula:

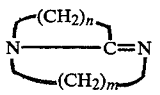

(wherein n=2 to 11 and m=2 to 6), such as 1,8-diazabicyclo[5,4,0]undecene-7,1,5-diazabycyclo[4,3,9]nonene, etc.;

imidazole derivatives such as 2-methylimidazole, 2-phenylimidazole, etc.;

imidazoline derivatives such as 2-methylimidazoline, 2-phenylimidazoline, etc.;

heterocyclic compounds such as oxazole, furazane, thiazole, indazole, purine, zanthine, naphthyridine, quinoxaline, etc. and the derivatives thereof.

(iv) Aromatic tertiary amines:

There are illustrated, for example, benzyldimethylamine, 2-(dimethylaminomethyl)phenol, 2,4,6-tris(dimethylaminomethyl)phenol, N,N-dimethylaniline, N,N,N',N'-tetramethyldiamino-diphenylmethane, N,N-dimethyltoluidine, etc.

In addition, salts or like derivatives of the above-described primary, secondary, and tertiary amine-type nitrogen atom-containing compounds can be used as well. For example, there are illustrated salts of mineral acids such as hydrochlorides, sulfates, etc., and organic acid salts such as 2-ethylhexanoates, acetates, etc. Further, there are salts between phenols (e.g., hydroquinone, phenol, bisphenol A, etc.) and these nitrogen-containing organic compounds. Specific examples thereof include triethylamine hydrochloride, 2,4,6-tris(dimethylaminomethyl)phenol 2-ethylhexanoate, laurylamine acetate, 1,8-diazabicyclo[5,4,0]undecene-7 phenolate, laurylamine acetate, etc.

As the quaternary ammonium salt-type nitrogen atom-containing organic compounds, there are illustrated those which are represented by the following general formula:

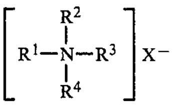

(wherein $R^1$, $R^2$, $R^3$, and $R^4$ each represents a monovalent hydrocarbyl group, which may be the same or different from each other, and X represents a halogen atom such as chlorine, bromine or iodine). The monovalent hydrocarbyl groups represented by $R^1$, $R^2$, $R^3$ and $R^4$ are usually an alkyl group containing 25 or less carbon atoms (e.g., a methyl group, an ethyl group, a butyl group, a hexadecyl group, an octyl group, a lauryl group, etc.), a cycloalkyl group (e.g., a cyclohexyl group, a cycloheptyl group, etc.), an aryl group (e.g., a phenyl group), an alkaryl group (e.g., a methylphenyl group, a dodecylphenyl group, etc.), or an arylalkyl group (e.g., a benzyl group, a phenylpropyl group, etc.). Specific examples of the quaternary ammonium salts represented by the above general formula include tetradthylammonium iodide, lauryltrimethylammonium chloride, distearyldimethylammonium chloride, alkylbenzyldimethylammonium chloride, etc.

As the other quaternary ammonium salts, there are illustrated those known as cationic active agents such as alkylamidomethylpyridinium chloride, laurylpicolinium chloride, etc.; those known as amphoteric active agents such as laurylbetaine, stearylbetaine, etc.; and anionic ion-exchange resins derived from polystyrene resin or the like.

Preferable ones of these various nitrogen atom-containing organic compounds are primary amine-type nitrogen atom-, secondary amine-type nitrogen atom-, tertiary amine-type nitrogen atom- and/or quaternary ammonium salt-type nitrogen atom-containing organic compounds and the derivatives thereof like salts, with tertiary amine-type nitrogen atom-containing organic compounds or the salts thereof and quaternary ammonium salt-type nitrogen atom-containing organic compounds being particularly preferable. A particularly preferable specific compound is tri-n-butylamine.

(c) Phosphorus-containing organic compounds selected from phosphine compounds and quaternary phosphonium salts Phosphine compounds are represented by the following general formula:

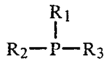

(wherein $R_1$, $R_2$, and $R_3$ each represents an alkyl group containing 1–25 carbon atoms, a cycloalkyl group, an aryl group, an alkaryl group or an arylalkyl group, which may be the same or different from each other), and include, for example, trimethylphosphine, triethylphosphine, triisopropylphosphine, tri-n-butylphosphine, tri-i-butylphosphine, tri-sec-butylphosphine, tris-2-ethylhexylphosphine, trioctylphosphine, trioctadecylphosphine, butyldiphenylphosphine, methylbutyloctylphosphine, dimethyloctylphosphine, triphenylphosphine, tricyclohexylphosphine, tribenzylphosphine, benzyldimethylphosphine, tris-2-phenylethylphosphine, tricyclopentylphosphine, dimethyllaurylphosphine, tritolylphosphine, tris-p-tert-butylphenylphosphine, etc.

Quaternary phosphonium salts are represented by the following general formula:

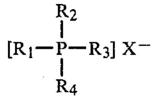

(wherein X represents a halogen atom selected from iodine, bromine and chlorine, and $R_1$, $R_2$, and $R_3$ each represents an alkyl group containing 1 to 25 carbon atoms, a cycloalkyl group, an aryl group, an alkaryl group or an arylalkyl group, which may be the same or different from each other), and include, for example, methyltriphenylphosphonium iodide, ethyltriphenylphosphonium iodide, propyltriphenylphosphonium iodide, n-butyltriphenylphosphonium iodide, n-decyltriphenylphosphonium iodide, methyltributylphosphonium iodide, ethyltriphenylphosphonium chloride, n-butyltriphenylphosphonium chloride, ethyltriphenylphosphonium bromide, tetrakishydroxymethylphosphonium chloride, tetraphenylphosphonium chloride, etc.

Of these, organophosphine compounds are preferable for the reasons that it is uniformly soluble in maleinized allo-ocimene and therefore facilitates control of reaction conditions, and that it is easily available.

(d) Thiocyanates

As thiocyanates, there are illustrated ammonium thiocyanate, sodium thiocyanate, potassium thiocyanate, magnesium thiocyanate, potassium thiocyanate, zinc thiocyanate, manganese thiocyanate, and the salts thereof with amines such as pyridine, quinoline, guanidine, toluidine, hydrazine, etc.

Of these, sodium thiocyanate is preferable.

(e) Solid Basic Compounds

Exemplary solid basic compounds include oxides such as calcium oxide, magnesium oxide, beryllium oxide, zinc oxide, silicon oxide, etc.; carbonates such as ammonium carbonate, barium carbonate, strontium carbonate, etc.; hydroxides such as sodium hydroxide, potassium hydroxide, magnesium hydroxide, barium hydroxide, etc.; and nitrous oxide-activated carbon, ammonia-activated carbon, etc.

Of these compounds of the above-described groups (a) to (e), sodium iodide and lithium bromide belonging to the group (a), and tri-n-butylamine belonging to the group (b) are preferable.

(3) Isomerization Conditions

Solid maleinized decatriene can easily be liquefied by heat-treating in the presence of the compound selected from the groups (a) to (e). As to heating temperature, too low temperature would require a long time for the liquefaction, whereas too high temperatures would predominantly cause decomposition reaction and resinous product-producing reaction, resulting in low yield of the intended liquefied product. Thus, reaction temperature is usually from 60° to 250° C., and preferably from 100° to 220° C. The heat-treating time cannot be generally specified because it depends upon the amount of catalyst and the reaction temperature but, usually, it is from 10 minutes to 10 hours, and preferably from 0.5 to 3 hours.

Amount of the isomerization catalyst to maleinized decatriene is 0.005 part by weight or more, preferably 0.01 to 3.0 parts by weight, per 100 parts by weight of the maleinized decatriene. Addition of the compound selected from the groups (a) to (e) may be conducted by adding the compound per se to heat-melted, maleinized decatriene or may be conducted according to other methods, for example, by dissolving it in a solvent such as water or acetone. Furthermore, the compound may be packed in a column by supporting on a carrier, through which a vapor of allo-ocimene may be passed at a desired reaction temperature to react.

Additionally, as is described above, the heat treatment can be continuously conducted by passing a maleinized allo-ocimene vapor through the column packed with the isomerization catalyst selected from the groups (a) to (e) and supported on a carrier such as pumice, active carbon, diatomaceous earth, silica gel, or molecular sieve at a given reaction temperature. In such case, the heat treatment is conducted in a short time at an elevated temperature of from 200° to 250° C.

The thus isomerized liquid product itself is stable, but, for raising the stability of the liquid product obtained by the isomerization treatment in the presence of the compound selected from the groups (b), (d) and (e) to the level of the liquid product obtained by the isomerization treatment in the presence of the compound selected from group (a), the product heat-modified in the presence of the compound selected from the groups (b), (d) and (e) is further heat-modified in the presence of an acidic catalyst or a noble metal catalyst to thereby more improve the liquid stability.

The exemplary acidic catalyst than can be used in this second-stage isomerization include polyphosphoric acid, boron trifluoride ethyl etherate, phosphorus pentoxide, sulfuric acid, phosphoric acid, phosphorus oxychloride, phosphorus pentachloride, acid sodium sulfate, pyrophosphosphoric acid, metaphosphoric acid, pyrosulfuric acid, chlorosulfonic acid, silica, alumina, acidic ion-exchange resin, aromatic sulfonic acid, acid clay, active clay, aluminum chloride, titanium tetrachloride, stannic chloride, boron trichloride, etc. and, as the noble metal catalyst, there are illustrated rhodium, ruthenium, palladium, etc.

As to heat-treating conditions of the second-stage isomerization, too low temperatures would require a long time for the liquefaction, whereas too high temperatures would predominantly cause decomposition reaction and resinous product-producing reaction, resulting in a low yield of the intended liquefied product. Reaction temperature, reaction time, and amount of catalyst cannot generally be specified, because they depend upon the kind of catalyst but, usually, reaction temperature in the second-stage reaction is from 50° to 250° C., and preferably from 100° to 220° C., heat-treating time is from 5 minutes to 8 hours, and preferably from 0.5 to 5 hours, and the amount of the catalyst is 0.001 part by weight or more per 100 parts by weight of maleinized decatriene with respect to the noble metal catalyst, from 1 to 15 parts by weight with respect to ion-exchange resins, silica, alumina, etc., and 0.1 to 5 parts by weight with respect to other acidic catalysts.

Additionally, maleinized decatriene will not be liquefied by merely heating in the presence of sulfuric acid or $BF_3$ etherate without conducting the isomerization in the presence of the compound selected from the groups (b), (d) and (e).

The product obtained by treating according to the process of the present invention can be used per se as an epoxy resin hardener but, for obtaining excellent cured materials, the product is preferably washed with water followed by distillation. For the purpose of decolorization, the product may be subjected to treatment with active carbon, addition of a filtration aid such as diatomaceous earth, or treatment with an appropriate disiccant for removing water, before the distillation.

Possibility of Industrial Exploitation of the Invention

The liquid product obtained by the process of the present invention can be used as an epoxy resin hardener and as an acid component of alkyd resin or unsaturated polyester resin, because it is in a liquid state at room temperatures. And, the product can be used as a rust inhibitor by converting to an amide, imide, ester, chlorine adduct, alkylene oxide adduct, or the like. Furthermore, as a salt of magnesium or aluminum, it can be used as a base oil for grease and, in the form of a diester, it can be used as a plasticizer for rubbers and resins (particularly vinyl chloride resin).

In particular, when used as a hardener for various epoxy resins [for example, epoxy resin represented by the following general formula:

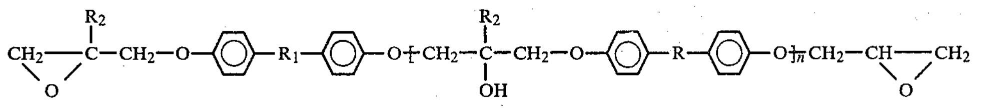

(wherein $R_1$ represents a divalent alkylene group containing 1 to 6 carbon atoms or one of the groups of —S—,

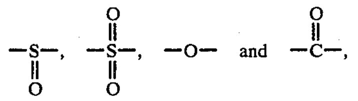
and $R_2$ represents —$CH_3$ or —H, and n represents a number of 0 to about 2), novolak type epoxy resin obtained from novolak type phenol resin and epichlorohydrin, epoxy resin obtained from phthalic acid and epichlorohydrin, epoxy resin obtained from p-hydroxybenzoic acid and epichlorohydrin, and epoxy resin obtained from an aromatic amine (e.g., toluidine or aniline) and epichlorohydrin], the product can exhibit excellent curing performance. In the case of using the liquid product as a hardener of epoxy resin, it is usually used in an amount of from 60 to 170 parts by weight, and preferably from 80 to 140 parts by weight, per 100 parts by weight of the epoxy resin.

And, in the case of using this liquid product as an epoxy resin hardener, other acid anhydride hardeners may, if necessary, be used in combination. For example, there are illustrated hexahydrophthalic anhydride, tetrahydrophthalic anhydride, methylhexahydrophthalic anhydride, methylnadic anhydride, phthalic anhydride, pyromellitic anhydride, dedecenylsuccinic anhydride, nadic anhydride, chlorendic anhydride, polycarboxylic acids primarily containing $C_{16-21}$ or $C_{36}$ dicarboxylic acid or tricarboxylic acid containing 54 carbon atoms, and the like.

Furthermore, in the case of using this liquid product as an epoxy resin hardener, a hardening accelerator may, if necessary, be used in combination. For example, there are used trialkylamine, N-dimethylbenzylamine, triethanolamine, piperidine, dimethylaminomethylphenol, tris(dimethylaminomethyl)phenol, tris(dimethylaminomethyl)phenol hexoate, imidazoles (for example, 2-ethyl-4-methylimidazole), dicyandiamide, triphenylphosphine, etc. as hardening accelerators. The hardening accelerators are used in amounts of 0.1 to 5 parts by weight per 100 parts by weight of the epoxy resin.

EXAMPLES AND APPLICATION EXAMPLES

The present invention will now be described by reference to Examples and Experiment Examples.

Preparation of maleinized allo-ocimene 686 g (7.0 moles) of maleic anhydride was placed in a 3 l four-necked flask equipped with a stirrer, thermometer, condenser, dropping funnel, and nitrogen-introducing pipe, and 100 cc of benzene was added thereto. 1000 g (0.735 mole) of allo-ocimene (made by Yasuhara Yushi Kogyo Co., Ltd.) was gradually added dropwise thereto at room temperature under stirring. The flask was cooled by a water bath to avoid increasing of the solution temperature due to heat of reaction, thus the reaction temperature being kept at 70° to 80° C. The dropwise addition of allo-ocimene was completed in about 1 hour. Further, in order to complete the reaction, the solution was stirred at 70°-80° C. for about 1 hour. Upon dropwise addition of allo-ocimene, the reaction solution appeared red and, as the reaction was completed, the color changed to slight brown.

After completion of the reaction, excess allo-ocimene and the solvent of benzene were distilled off at temperatures of 100° C. or lower than that with suction by an aspirator (degree of reduction pressure: 20 mmHg).

Maleinized allo-ocimene thus formed had a melting point of 75° to 80° C. and was solid at normal temperatures.

EXAMPLE 1

60 g of maleinized allo-ocimene obtained in the above preparation example was placed in a four-necked flask equipped with a stirrer, thermometer, condenser, and nitrogen-introducing pipe, and heated to about 100° C. to melt. 1.8 g of sodium iodide was added thereto, followed by stirring at 200° C. for 2 hours. Sodium iodide was not completely dissolved therein but was finely dispersed.

After completion of the reaction, 50 cc of methyl isobutyl ketone was added thereto, and the resulting mixture was washed with 50 cc of a 10% sodium thiosulfate aqueous solution. After washing with water, the aqueous layer was removed, and a desiccant of sodium sulfate was added thereto to dehydrate, followed by simple distillation at a reduced pressure of 0.5 mmHg. Thus, 56 g (yield: 93%) of pale yellow, liquid maleinized allo-ocimene was obtained as a fraction of distillate boiling at 160° to 185° C./0.5 mmHg.

This liquid maleinized allo-ocimene did not crystallized when left in a 5° C. refrigerator, −20° C. refrigerator, or at normal temperatures (20° to 25° C.) for not shorter than two months. It has a viscosity (measured by means of model-E viscometer) of 125 cps at 25° C.

EXAMPLES 2 to 14

Solid maleinized allo-ocimene was heat-treated in the same manner as described in Example 1 except for changing the kind and the amount of catalyst, reaction time, reaction temperature, and manner of addition of catalyst as shown in Table 1.

The thus obtained liquid maleinized allo-ocimene had a viscosity as shown in Table 2 and was obtained in a yield also given in Table 2.

Additionally, in Examples 9 to 14, the catalysts were uniformly dissolved but, in other Examples, part of the catalysts were dispersed without being dissolved.

Every liquid maleinized allo-ocimene (purified by distillation) obtained in each Example was excellent in liquid stability and, when stored for not shorter than 2 months at 5° C., −20° C., or 20°-25° C., no crystals were formed.

TABLE 1

| Example | Kind of Catalyst | Amount of Catalyst (%)*1 | Manner of Adding Catalyst | Temperature/ Reaction Time |
|---|---|---|---|---|
| 1 | NaI | 3 | added per se | 200° C./2 hrs. |
| 2 | " | " | " | 180° C./4 hrs. |
| 3 | " | " | " | 220° C./1 hr. |
| 4 | KI | " | " | 200° C./2 hrs. |
| 5 | NaI | 6 | " | " |
| 6 | " | 3 | " | 160° C./4.5 hrs. & 200° C./2 hrs. |
| 7 | " | " | " | 140° C./3 hrs. & 200° C./1.5 hrs. |
| 8 | " | 0.33 | added as a 50% aqueous solution | 200° C./1 hr. |
| 9 | " | 0.066 | added as a 10% aqueous solution | " |
| 10 | KI | " | added as a 10% aqueous solution | " |
| 11 | NaI | 0.020 | added as a 4% aqueous solution | " |
| 12 | " | " | added as a 4% aqueous solution | " |
| 13 | " | " | added as a 4% acetone solution | " |
| 14 | " | " | added as a 4% acetone solution | 180° C./4 hrs. |

TABLE 1-continued

Note:
*1 percent by weight based on starting maleinized allo-ocimene

TABLE 2

| Example | Viscosity of Liquid Product*2 | Yield of Liquid Product (%) |
|---|---|---|
| 1 | 125 | 93 |
| 2 | 174 | 96 |
| 3 | 128 | 91 |
| 4 | 130 | 94 |
| 5 | 126 | 93 |
| 6 | 165 | 93 |
| 7 | 145 | 92 |
| 8 | 206 | 91 |
| 9 | 183 | 93 |
| 10 | 175 | 93 |
| 11 | 197 | 93 |
| 12 | 132 | 94 |
| 13 | 127 | 94 |
| 14 | 195 | 93 |

Note:
*2 cps (at 25° C.)

EXAMPLE 15

60 g of solid maleinized allo-ocimene was placed in a four-necked flask equipped with a stirrer, thermometer, condenser, and nitrogen-introducing pipe, and heated to about 100° C. to melt. To this was added 0.06 g of lithium bromide monohydrate, followed by stirring at 200° C. for one hour. Lithium bromide was not completely dissolved, and was finely dispersed.

After completion of the reaction, the reaction mixture was subjected to simple distillation at a reduced pressure of 0.5 mmHg. Thus, 55 g (yield: 92%) of pale yellow liquid maleinized allo-ocimene was obtained as a fraction of distillate boiling at 150° to 165° C./0.9 mmHg.

When left for not shorter than two months in a 5° C. refrigerator, −20° C. refrigerator, or at normal temperatures (20° to 25° C.), the liquid maleinized allo-ocimene did not crystallize in every case. It had a viscosity of 176 cps at 25° C. (measured by means of a model-E- viscometer).

EXAMPLES 16 to 20

Solid maleinized allo-ocimene was liquefied in the same manner as in Example 15 except for changing the kind and the amount of catalyst, reaction time, and reaction temperature as shown in Table 3.

Viscosity (at 25° C.) and yield with respect to each of the thus obtained liquid products are tabulated in the same table. Additionally, the liquid product obtained in each Example showed the same liquid stability as the liquid product obtained in Example 15.

TABLE 3

| Example | Catalyst | Amount of Catalyst (%) | Reaction Temperature (°C.) | Reaction Time (hr) | Viscosity (cps) | Yield (%) |
|---|---|---|---|---|---|---|
| 15 | $LiBr \cdot H_2O$ | 0.1 | 200 | 1 | 176 | 92 |
| 16 | $LiBr \cdot H_2O$ | 0.03 | 200 | 1 | 142 | 95 |
| 17 | NaBr | 0.3 | 200 | 1 | 140 | 91 |

TABLE 3-continued

| Example | Catalyst | Amount of Catalyst (%) | Reaction Temperature (°C.) | Reaction Time (hr) | Viscosity (cps) | Yield (%) |
|---|---|---|---|---|---|---|
| 18 | KBr | 0.3 | 200 | 2 | 153 | 92 |
| 19 | LiBr . $H_2O$ | 0.1 | 140 | 3 | 165 | 90 |
| 20 | LiBr . $H_2O$ | 0.2 | 220 | 0.25 | 185 | 88 |

EXAMPLE 21

60 g of solid maleinized allo-ocimene was placed in a four-necked flask equipped with a stirrer, thermometer, condenser, and nitrogen-introducing pipe, and heated to about 100° C. to melt. 0.3 g of tri-n-butylamine was added thereto and, while introducing thereinto nitrogen, the mixture was stirred at 190° C. for 1 hour during which tri-n-butylamine was uniformly dissolved.

The thus treated product was subjected to simple distillation at a reduced pressure of 0.5 mmHg to obtain 57 g (yield based on the starting maleinized allo-ocimene: 95%) of pale yellow, liquid maleinized allo-ocimene as a fraction of distillate boiling at 147° to 175° C./0.5 mmHg. This had a viscosity (measured by means of a model-E viscometer) of 87 cps at 25° C.

This liquid maleinized allo-ocimene did not crystallize when left at normal temperatures (20° to 25° C.) for two weeks or longer, or when left in a refrigerator (5° C.) for 5 days. However, a mixture prepared by adding 0.1 g of maleinized allo-ocimene before the liquefying treatment to 10 g of this liquid maleinized allo-ocimene was left in a refrigerator (5° C.), the mixture crystallized after 3 days.

EXAMPLE 22 to 30

In the same manner as in Example 4 except for using maleinized allo-ocimene prepared in the same manner as in Example 21 and variously changing the kind and the amount of nitrogen atom-containing organic compound, reaction temperature, and reaction time, liquefaction treatment of the maleinized allo-ocimene was conducted. Results thus obtained are tabulated in Table 4.

TABLE 4

| Example | Nitrogen Atom-Containing Organic Compound: Kind | Amount Used (%) | Reaction Temperature/ Time | Liquid Product: Viscosity (cps) | Yield (%) |
|---|---|---|---|---|---|
| 21 | tri-n-butylamine | 0.5 | 190° C./1 hr | 87 | 95 |
| 22 | triethanolamine | 1.0 | 200° C./1.5 hrs | 98 | 92 |
| 23 | triethylamine hydrochloride | 1.0 | 200° C./1 hr | 92 | 94 |
| 24 | cetyltrimethylammonium bromide | 1.0 | 180° C./1 hr | 90 | 93 |
| 25 | Triethylenetetramine | 1.5 | 200° C./2 hrs | 103 | 90 |
| 26 | 1,8-diazabicyclo [5,4,0]undecene-7 | 0.05 | 190° C./1 hr | 95 | 94 |
| 27 | 1,8-diazabicyclo-[5,4,0]undecene-7 | 0.5 | 140° C./1 hr | 88 | 95 |
| 28 | tri-n-butylamine | 0.5 | 150° C./0.5 hr | 93 | 94 |
| 29 | isoquinoline | 1.0 | 200° C./2 hrs | 110 | 93 |
| 30 | 2,4,6-tris(dimethyl-aminomethyl)phenol 2-ethylhexanoate | 1.0 | 200° C./1 hr | 100 | 93 |

EXAMPLE 31

69 g (0.7 mole) of maleic anhydride was placed in a 200 ml four-necked flask equipped with a stirrer, thermometer, condenser, dropping funnel, and nitrogen-introducing pipe, heated to 130° to 140° C. while stirring and introducing thereinto a nitrogen gas and, while maintaining the temperature at the above-described level, a mixture solution of 50 g (0.37 mole) of allo-ocimene and 100 g (0.37 mole) of 50% -terpinene (made by Yasuhara Yushi Kogyo Co., Ltd.) was gradually added dropwise thereto. The dropwise addition was completed in about one hour, followed by stirring for 10 hours. A product obtained by purifying the thus obtained product through distillation at a reduced pressure of 20 mmHg, i.e., a mixed acid anhydride composed of maleinized allo-ocimene and maleinized-terpinene was in a liquid state immediately after preparation but, after 3 days, it crystallized.

0.8 g (0.5 wt% based on the theoretical yield of the acid anhydride mixture) of tri-n-butylamine was added to the thus obtained mixture of maleinized allo-ocimene and maleinized-terpinene, followed by stirring at 190° C. for 0.5 hour. The resulting product was subjected to simple distillation at a reduced pressure of 0.5 mmHg to obtain 150 g (yield: 91%) of the pale yellow, liquid acid anhydride mixture as a fraction of distillate boiling at 155° to 180° C./0.5 mmHg. This had a viscosity of 260 cps at 25° C.

This liquid acid anhydride mixture was stored in a stable liquid state for 2 months or longer at normal temperature (20° to 25° C.), in a 5° C. refrigerator, or in a −20° C. refrigerator. When 0.1 g of solid maleinized allo-ocimene crystals were added to 10 g of this liquid acid anhydride mixture and left in a refrigerator (5° C.), the mixture was similarly in a stable liquid state for 2 months or longer than that.

EXAMPLES 32 to 35

Maleinizing reaction was conducted in the same manner as in Example 31 except for dropping a mixture solution of allo-ocimene and α-terpinene (the same one as used in Example 31) or myrcene (purity: 75%) with various mixing proportions as described in Table 5 in place of the mixed solution dropped in Example 31, and the resulting maleinized products were subjected to the same isomerization reaction.

Viscosity and yield with respect to each of liquefied acid anhydride mixtures are shown in Table 5. When the liquid acid anhydride mixtures were subjected to the same stability test as in Example 31, all of them were found to be stably maintained in a liquid state for 2 months or longer than that.

TABLE 5

| Ex-am-ple | Mixing Proportion of Starting Unsaturated Hydrocarbons (wt %) | | | Liquefied Product | |
|---|---|---|---|---|---|
| | Allo-ocimene | α-Terpinene*1 | Myrcene*2 | Vis-cosity (cps)*3 | Yield (wt %) |
| 31 | 50 | 50 | — | 260 | 92 |
| 32 | 50 | — | 50 | 105 | 90 |
| 33 | 60 | 40 | — | 222 | 93 |
| 34 | 70 | — | 30 | 112 | 92 |
| 35 | 30 | 70 | — | 350 | 87 |

Notes:
*1 Numerals in this column are obtained by converting a 50%-pure α-terpinene solution to a 100% solution.
*2 Numerals in this column are obtained by converting a 75%-pure myrcene solution to a 100% solution.
*3 Measured at 25° C.

EXAMPLE 36

To 200 g of liquid maleinized allo-ocimene obtained in Example 21 was added 16 g of powdery silica alumina N-631 L (trade name; made by Nippon Gas Chemistry Co., Ltd.) and, after stirring for 4 hours at 180° C., the mixture was cooled to room temperature. Then, 150 ml of methyl isobutyl ketone was added thereto, and insolubles of silica, alumina, etc. were removed by filtration. Further, methyl isobutyl ketone in the solubles was removed by means of an evaporator.

Then, the residue was distilled under reduced pressure to obtain 170 g (yield: 85%) of a fraction of distillate boiling at a reduced pressure of 1.5 mmHg.

This liquid maleinized allo-ocimene had a viscosity of 125 cps at 25° C. This liquid product kept the liquid state after being stored for 2 months in thermostatic chambers controlled to 20° C., 5° C., and −20° C., respectively.

Furthermore, when 10 g of this liquid product was admixed with 0.1 g of solid maleinized allo-ocimene, the mixture kept the liquid state after being stored for 2 months in a 5° C. thermostatic chamber.

EXAMPLES 37 to 42

200 g of the liquid maleinized allo-ocimene obtained in Example 21 was subjected to second-stage isomerization using various acidic catalysts as second-stage isomerization catalysts in the same manner as in Example 36 except for selecting the amount of the catalyst, second-stage treatment temperature, treating time, and after-treatment as shown in Table 6.

Viscosities of the liquid products at 25° C. and results of the liquid stability tests on four items as in Example 31 are tabulated in Table 6 together with the yields.

TABLE 6

| Expl | Second-Stage Catalyst | Amount of Catalyst (g) | Reaction Temp. (°C.) | Reaction Time (hr) | After-Treatment | Viscosity of Product (cps) | Yield (%) | Liquid Stability |
|---|---|---|---|---|---|---|---|---|
| 37 | Silica Alumina | 16 | 200 | 1 | Filtration | 120 | 89 | Stable with respect to every item |
| 38 | Polyphosphoric acid | 1 | 160 | 2 | Washing with water* | 118 | 92 | Stable with respect to every item |
| 39 | $BF_3$—etherate** | 10 | 100 | 3 | Washing with water* | 120 | 91 | Stable with respect to every item |
| 40 | $P_2O_5$ | 6 | 160 | 2 | None | 115 | 90 | Stable with respect to every item |
| 41 | $H_2SO_4$ | 2 | 150 | 6 | Washing with water* | 120 | 87 | Stable with respect to every item |
| 42 | Ion-exchange resin*** | 20 | 120 | 4 | Filtration | 120 | 88 | Stable with respect to every item |

Notes:
*After adding 150 ml of methyl isobutyl ketone, 100 ml of water was further added to wash with, and the separated aqueous layer was distilled under reduced pressure.
**Content of $BF_3$: 47 wt %
***Amberlyst 15 (trade name; made by Rohm & Haas Co.)

EXAMPLE 43

60 g of solid maleinized allo-ocimene was placed in a four-necked flask equipped with a stirrer, thermometer, condenser, and nitrogen-introducing pipe and, under stirring while introducing thereinto a nitrogen stream, it was heated to 180° C. to melt. 0.3 g of triphenylphosphine was added thereto, and heating was conducted up to 190° C., followed by reacting at the same temperature for one hour.

Then, a pale yellow fraction of distillate boiling at 145° to 175° C. at a reduced pressure of 0.5 mmHg (yield: 90%) was obtained through distillation.

This liquid maleinized allo-ocimene had a viscosity of 92 cps at 25° C. This did not crystallize but kept the liquid state when stored for 2 weeks at 20° C.

When 0.1 g of solid maleinized allo-ocimene was added to 10 g of this liquid compound, it crystallized after being stored for 3 days in a 5° C. thermostatic chamber.

EXAMPLE 44

16 g of powdery silica alumina, N-631 L (trade name; containing 87% silica and 13% alumina; made by Nippon Gas Chemistry Co., Ltd.) was added to 200 g of liquid maleinized allo-ocimene obtained in Example 43 and, after stirring for 4 hours at 180° C., the mixture was cooled to room temperature. Then, 150 ml of methyl isobutyl ketone was added to filtrate off insolubles of silica, alumina, etc., and methyl isobutyl ketone in the solubles was in turn removed by using an evaporator.

Then, the residue was distilled under reduced pressure to obtain 170 g (yield: 83%) of a fraction of distillate boiling at a reduced pressure of 1.5 mmHg.

This liquid maleinized allo-ocimene had a viscosity of 125 cps at 25° C., and kept the liquid state after being stored for 2 months in thermostatic chambers controlled to 20° C., 5° C., and −20° C., respectively.

Furthermore, a mixture composed of 10 g of this liquid compound and 0.1 g of solid maleinized allo-ocimene kept the liquid state after being stored for 2 months in a 5° C. thermostatic chamber.

EXAMPLES 45 to 48

Solid maleinized allo-ocimene was liquefied in the same manner as in Example 43 except for selecting the kind and the amount of phosphorus-containing organic compound, reaction temperature, and reaction time as shown in Table 7.

Yields, viscosities at 25° C., and liquid stability upon being stored for 2 weeks at normal temperatures of the thus obtained liquid products are tabulated in the same table as well.

TABLE 7

| Example | Catalyst | Amount of Catalyst (parts by weight)* | Temperature (°C.) | Reaction (hr) | Viscosity (cps) | Yield (%) | Liquid Stability |
|---|---|---|---|---|---|---|---|
| 45 | tri-n-butyl-phosphine | 0.5 | 190 | 1 | 90 | 91 | stable |
| 46 | triphenyl-phosphine | 1.0 | 140 | 2 | 103 | 88 | " |
| 47 | tri-n-butyl phosphine | 0.05 | 200 | 2 | 98 | 90 | " |
| 48 | tetraphenyl-phosphonium chloride | 0.5 | 190 | 1 | 90 | 88 | " |

Note:
*Amount per 100 parts by weight of maleinized allo-ocimene.

EXAMPLE 49

69 g of maleic anhydride was placed in the same four-necked flask as used in Example 43 and, while stirring under a nitrogen stream, heated to 140° C. Then, a mixture of 50 g of allo-ocimene and 100 g of 50%-pure-terpinene was added dropwise thereto in one hour with maintaining the temperature at 140° C., followed by stirring for 10 minutes at the same temperature.

Thereafter, 0.8 g of triphenylphosphine was added to the inside of the flask and, after raising the temperature to 190° C., stirring was continued for 30 minutes at the same temperature to complete the isomerization.

After completion of the reaction, distillation yielded 145 g (yield: 88%) of a pale yellow fraction of distillate boiling at 155° to 180° C. at a reduced pressure of 0.5 mmHg. This liquid product had a viscosity of 270 cps at 25° C., and kept the liquid state after being stored for 2 months in thermostatic chambers controlled at 20° C., 5° C., and −20° C., respectively.

Furthermore, a mixture composed of 10 g of this liquid compound and 0.1 g of solid maleinized allo-ocimene kept the liquid state after being stored for 2 months in a 5° C. thermostatic chamber.

EXAMPLES 50 and 51

Isomerization treatment was conducted in the same manner as in Example 49 except for using allo-ocimene and α-terpinene in the proportions given in Table 8, and stability and viscosity of each of the thus obtained pale yellow liquid products were measured. The results are tabulated in Table 8 together with the yields.

EXAMPLES 52 AND 53

Isomerization treatment was conducted in the same manner as in Example 49 except for using 75%-pure myrcene in place of α-terpinene in the proportions given in Table 8, and the stability and viscosity at 25° C. of each of the thus obtained pale yellow liquid products were measured. The results are given in Table 8 together with the yields.

Additionally, 10 g of each of the liquid products obtained in Examples 49 to 53 was admixed with 0.1 g of solid maleinized allo-ocimene, and the mixture was stored for 2 months in a 5° C. thermostatic chamber to observe liquid stability. Thus, all mixtures were found to keep the liquid state.

TABLE 8

| | | | | | | Product | | | |
|---|---|---|---|---|---|---|---|---|---|
| | | | | | | | Storage Stability | | |
| Expl | Allo-ocimene (g) | α-Terpinene (g)*1 | Myrcene (g)*2 | Yield (%) | Viscosity (cps) | 20° C. | 5° C. | −20° C. | Crystal nuclei were added. |
| 49 | 50 | 50 | — | 88 | 270 | stable | stable | stable | stable |
| 50 | 90 | 60 | — | 90 | 225 | " | " | " | " |
| 51 | 45 | 105 | — | 87 | 360 | " | " | " | " |
| 52 | 105 | — | 45 | 89 | 110 | " | " | " | " |
| 53 | 75 | — | 75 | 90 | 110 | " | " | " | " |

Notes:
*1Numerals in this column are obtained by converting a 50%-pure α-terpinene solution to a 100%-pure solution.
*2Numerals in this column are obtained by converting a 75%-pure myrcene solution to a 100%-pure solution.

EXAMPLES 54 TO 58

Solid maleinized allo-ocimene was subjected to the same liquefying treatment as in Example 43 except for using the compounds given in Table 9 in amounts also given there in place of 0.9 g of triphenylphosphine and employing the isomerization temperature and treating time given in Table 9, and the viscosity at 25° C. and the liquid stability of the resulting liquid products after being stored for 2 hours in a 20° C. thermostatic chamber were measured. The results thus obtained are given in Table 9 together with yields.

TABLE 9

| Expl | Catalyst | Amount of Catalyst (g) | Isomerization Temperature (°C.) | Isomerization Time (hr) | Product Yield (%) | Product Viscosity (cps) | Product Liquid Stability |
|---|---|---|---|---|---|---|---|
| 54 | NaSCN | 0.6 | 150 | 3 | 90 | 107 | Stable |
| 55 | LiCl | 1.2 | 200 | 1 | 83 | 95 | " |
| 56 | $CH_3COONa$ | 0.6 | 200 | 0.5 | 80 | 88 | " |
| 57 | LiCl | 0.12 | 200 | 3 | 85 | 98 | " |
| 58 | MgO | 0.6 | 200 | 1 | 87 | 110 | " |

EXAMPLE 59

In the same manner as in Example 49 except for using 3.3 g of LiCl in lieu of 0.8 g of triphenylphosphine and employing the isomerization conditions of 200° C. and 1 hour in place of 190° C. and 30 minutes, there was obtained a pale yellow liquid product (yield: 85%). This product had a viscosity of 275 cps at 25° C. and, when stored in 20° C., 5° C., and −20° C. thermostatic chambers, it kept the liquid state in every case.

Furthermore, a mixture of 10 g of this liquid compound and 0.1 g of solid maleinized allo-ocimene kept a liquid state even after being stored for 2 months in a 5° C. thermostatic chamber.

EXAMPLE 60

In the same manner as in Example 59 except for changing the amounts of allo-ocimene and -terpinene to 90 g and 60 g, respectively, there was obtained a pale yellow liquid product (yield: 82%). This liquid product had a viscosity of 230 cps at 25° C. Liquid stability with respect to the above-described four items indicated that it kept the liquid state even after 2 months.

EXAMPLE 61

In the same manner as in Example 60 except for using myrcene in place of -terpinene, there was obtained a pale yellow liquid product (yield: 88%). This had a viscosity of 100 cps at 25° C.

Liquid stability with respect to the 4 items indicated that it kept the liquid state even after two months.

EXAMPLE 62

In the same manner as in Example 61 except for using 105 g of allo-ocimene and 45 g of myrcene, there was obtained a pale yellow liquid product (yield: 90%). This had a viscosity of 120 cps at 25° C.

And, liquid stability with respect to the four items indicated the liquid state even after 2 months.

EXAMPLES 63 TO 65

Re-isomerization with acidic catalysts was conducted in the same manner as in Example 44 except for using the liquid maleinized allo-ocimene obtained in Examples 54, 55 and 58 in place of the maleinized allo-ocimene obtained in Example 43.

Viscosities of the thus obtained liquid compounds are shown in Table 10 together with the yields and the liquid stability with respect to 4 items.

TABLE 10

| Example | First-Stage Catalyst | Second-Stage Catalyst | Product Yield (%) | Product Viscosity (cps) | Product Liquid Stability |
|---|---|---|---|---|---|
| 63 | NaSCN | Silica Alumina | 83 | 125 | Kept the liquid state after 2 months in every case |
| 64 | LiCl | Silica Alumina | 86 | 127 | Kept the liquid state after 2 months in every case |
| 65 | MgO | Silica Alumina | 80 | 120 | Kept the liquid state after 2 months in every case |

EXAMPLES 66 TO 68

In the same manner as in Example 44 except for using 200 g of the liquid maleinized allo-ocimene obtained in Example 43, using various acidic catalysts given in Table 11 as the second-stage isomerization catalysts, and employing the amounts of the catalysts, second-stage isomerization temperature, isomerization time, and after-treatments given in Table 11, there were obtained liquid products.

Viscosity of the liquid products at 25° C. and the results of the liquid stability tests on four items are given in Table 11 together with the yield.

TABLE 11

| Expl | Second-Stage Catalyst | Amount of Catalyst (g) | Reaction Temp. (°C.) | Reaction Time (hr) | After-Treatment | Viscosity of Product (cps) | Yield (%) | Liquid Stability |
|---|---|---|---|---|---|---|---|---|
| 66 | Polyphosphoric acid | 1 | 160 | 2 | Washing with water* | 115 | 90 | Stable with every item |
| 67 | Sulfuric acid | 2 | 150 | 6 | Washing with water* | 120 | 85 | Stable with every item |
| 68 | Ion-exchange resin** | 20 | 120 | 4 | Filtration | 120 | 87 | Stable with every item |

Notes:
*After adding 150 ml of methyl isobutyl ketone, 100 ml of water was further added thereto to wash with, and the separated aqueous layer was distilled under reduced pressure.
**Amberlyst 15 (trade name; made by Rohm & Haas Co.)

EXAMPLES 69 TO 71

A Diels-Alder reaction product between 2,6-dimethyl-1,3,6-octatriene and maleic anhydride (m.p. 60° C.) was subjected to the same liquefaction reaction as in Example 15 under the conditions given in Table 12.

Viscosity at 25° C. and yield of the thus obtained liquid products are also given in Table 12.

TABLE 12

| Example | Catalyst | Amount of Catalyst (%) | Reaction Temperature (°C.) | Reaction Time (hr) | Viscosity (cps) | Yield (%) |
|---|---|---|---|---|---|---|
| 69 | LiBr . $H_2O$ | 0.1 | 200 | 1 | 190 | 93 |
| 70 | LiBr . $H_2O$ | 0.03 | 200 | 2 | 193 | 95 |
| 71 | NaBr | 0.3 | 200 | 2 | 197 | 91 |

This composition had a viscosity of about 20 poises at 25° C., and hence casting and the like were conducted extremely easily.

This resin composition was pre-cured for 3 hours at 80° C., then post-cured for 6 hours at 120° C. to obtain tough cured resin as shown in Table 13.

For comparison, formulation of epoxy resin compositions containing known hardeners and physical properties of the cured resins are also given in Table 13.

TABLE 13

| | | *1 | *2 | *3 |
|---|---|---|---|---|
| Formulation | Epikote 828 (parts by weight) | 100 | 100 | 100 |
| | Hardener (parts by weight) | 115 | 80 | 140 |
| | BDMA*4 (parts by weight) | 1 | 1 | 1 |
| Mechanical Properties | tensile strength*5 ($kg/cm^2$) | 5.8 | 6.2 | 5.1 |
| | bending strength*6 ($kg/cm^2$) | 11.5 | 12.8 | 8.2 |
| | thermal deformation temperature*7 (°C.) | 114 | 118 | 62 |
| | thermal shock resistance*8 (crack resistance) | 1 | 0 | 5 |
| Electric Properties | Dielectric constant (ε)*9 | | | |
| | 60 Hz | 3.05 | 2.93 | — |
| | 1 KHz | 3.01 | 2.93 | — |
| | 100 KHz | 2.98 | 2.95 | — |
| | 1 MHz | 2.98 | 3.05 | — |

Notes:
*1 Composition of Experiment 1
*2 Comparative composition 1; containing hexahydrophthalic anhydride as a hardener.
*3 Comparative composition 2; containing as a hardener commercially available dodecenylsuccinic anhydride (trade name: DSA; made by Sanyo Chemical Industry Co. Ltd.) represented by the following general formula:

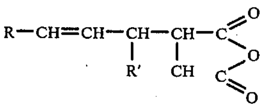

wherein R and R' each represents an alkyl group or a hydrogen atom, with the sum of carbon atoms in R and R' being 9.
*4 benzyldimethylamine (accelerator)
*5 measured according to ASTM D-638-52T
*6 measured according to ASTM D-790-49T
*7 measured according to ASTM D-648-45T
*8 measured according to a ½ hexagon nut method (according to Oliphant Washer method)
*9 measured according to ASTM D-150-54T

EXAMPLE 72

60 g of a solid Diels-Alder reaction adduct between 2,6-dimethyl-1,3,6-octatriene and maleic anhydride was placed in a four-necked flask equipped with a stirrer, thermometer, condenser, and nitrogen-introducing pipe, and heated to about 80° C. to melt. 0.3 g of tri-n-butylamine was added thereto and, while introducing thereinto nitrogen at 180° C., the mixture was stirred for 2 hours. Tri-n-butylamine was uniformly dissolved therein. The thus treated product was subjected to simple distillation at a reduced pressure of 1 mmHg, and 54 g (yield: 90%) of pale yellow liquid maleinized allo-ocimene was obtained as a fraction of distillate boiling at 162° to 178° C./1.0 mmHg. This had a viscosity of 210 cps at 25° C.

This liquid product was in a liquid state over 2 months when it was subjected to the same liquid stability test as in Example 31.

Application Examples as Epoxy Resin Hardener

Experiment 1

100 Parts (by weight, hereinafter the same) of Epikote 828 [epoxy equivalency: 189; trade name of glycidyl ether of 2,2-bis-(4-hydroxyphenyl)propane; made by Shell International Chemicals Corp.], 115 parts of liquid maleinized allo-ocimene obtained in Example 1, and 1 part of a hardening accelerator of benzyldimethylamine were uniformly mixed at a normal temperature and defoamed under reduced pressure (not more than 2 mmHg) to prepare an epoxy resin composition.

As is apparent from the results in Table 13, the epoxy resin composition of Experiment 1 showed a high thermal deformation temperature though the hardener contained a short side chain of butenyl group. That is, the thermal deformation temperature of the composition obtained in Experiment 1 was higher than that of comparative composition 2 using a hardener having a long alkyl group as side chain by about 50° C.

And, as compared to comparative composition 1 using hexahydrophthalic anhydride as a hardener, the composition of this Experiment 1 showed a high crack resistance. This may be attributed to a possible rise in flexibility due to the presence of butenyl group in the side chain of liquid maleinized allo-ocimene.

Further, as to the mechanical and electric properties of cured products, the composition of Experiment 1 is by no means inferior to the comparative composition 1 using hexahydrophthalic anhydride as a hardener.

Experiment 2

100 Parts (by weight, hereinafter the same) of Epikote 828 [trade name of 2,2-bis-(4-hydroxyphenyl)propane glycidyl ether; epoxy equivalency: 189; made by Shell International Chemicals Corp.] as admixed with 120 parts of the liquefied product of maleinized all-ocimene obtained in Example 21 (as a hardener) and 2 parts of an accelerator of benzyldimethylamine, and defoamed under a reduced pressure of 2 mm Hg to prepare an epoxy resin composition.

This composition had a viscosity of about 19 poises at 25° C., and casting of the composition was conducted with extreme ease.

When this resin composition was pre-cured for 3 hours at 80° C., then post-cured for 6 hours at 120° C., there was obtained a tough cured resin shown in Table 14.

Experiment 3

In the same manner as in Experiment 2 except for using as a hardener 90 parts of the liquid product of a mixture of maleinized allo-ocimene and maleinized teripnene obtained in Example 31, the epoxy resin was cured. The results thus obtained are given in Table 14.

Experiment 4

In the same manner as in Experiment 2 except for using as a hardener 130 parts of the liquid product of a mixture of maleinized allo-ocimene and maleinized myrcene obtained in Example 34, the epoxy resin was cured. The results thus obtained are given in Table 14.

Experiment 5

In the same manner as in Experiment 2 except for using as a hardener the liquid maleinized allo-ocimene obtained in Example 37, the epoxy resin was cured.

The results thus obtained are given in Table 14.

TABLE 14

| | | Experiment No. | | | |
|---|---|---|---|---|---|
| | | 2 | 3 | 4 | 5 |
| Resin Formulation (parts by weight) | Epikote 828 | 100 | 100 | 100 | 100 |
| | Hardener | | | | |
| | Liquid product of Example 21 | 120 | — | — | — |
| | Mixed liquid product of Example 31 | — | 90 | — | — |
| | Mixed liquid product of Example 34 | — | — | 130 | — |
| | Liquid product of Example 37 | — | — | — | 120 |
| | Accelerator (benzyldimethylamine) | 2 | 2 | 2 | 2 |
| Physical Properties of Cured Resin | Bending strength ($kg/cm^2$) | 14.3 | 14.0 | 14.0 | 14.0 |
| | Bending modulus of elasticity ($kg/cm^2$) | 310 | 310 | 300 | 300 |
| | Thermal deformation temperature (°C.) | 123 | 111 | 115 | 115 |
| | Thermal shock resistance (crack resistance) | 1 | 1 | 1 | 1 |
| | Dielectric coefficient | | | | |
| | 23° C. 50 Hz | 3.3 | 3.5 | 3.2 | 3.3 |
| | 1 KHz | 3.2 | 3.5 | 3.2 | 3.2 |
| | 100 KHz | 3.2 | 3.4 | 3.1 | 3.2 |
| | Water resistance (weight increase %) | 0.35 | 0.38 | 0.33 | 0.32 |

Experiments 6 to 11

100 parts by weight of an epoxy resin, "Epikote 828" (trade name; made by Shell International Chemicals Corp.; epoxy equivalency: 189) was admixed with 2 parts by weight of a hardening accelerator of benzyldimethylamine and a hardener of the liquid maleinized allo-ocimene obtained in each Example shown in Table 15 in an amount given in the same table and, after uniformly stirring to mix at a normal temperature, defoamed under a reduced pressure of not more than 2 mm Hg to prepare epoxy resin compositions.

This resin composition was preliminary cured for 3 hours at 80° C. Then, the temperature was raised to 120° C. and was kept at the same level for 6 hours to completely cure the composition.

Physical properties of the thus obtained cured products are tabulated in Table 15 together with the data of viscosity of the epoxy resin composition at 25° C. before being cured.

TABLE 15

| | | | Experiment Example | | | | | |
|---|---|---|---|---|---|---|---|---|
| Maleinized allo-ocimene | | | 6<br>Ex.43 | 7<br>Ex.50 | 8<br>Ex.55 | 9<br>Ex.59 | 10<br>Ex.54 | 11<br>Ex.52 |
| Compounded amount (parts by weight) | | | 120 | 90 | 120 | 90 | 120 | 130 |
| Viscosity of epoxy resin composition (cps) | | | 950 | 2300 | 980 | 2250 | 1000 | 670 |
| Physical properties of cured product | bending strength ($kg/cm^2$) | | 14.0 | 13.8 | 14.0 | 13.5 | 13.2 | 13.5 |
| | bending modulus of elasticity ($kg/cm^2$) | | 310 | 320 | 310 | 300 | 320 | 320 |
| | thermal deformation temperature (°C.) | | 121 | 110 | 122 | 110 | 123 | 112 |
| | shock resistance | | 1 | 1 | 1 | 1 | 1 | 1 |
| | dielectric constant | 50 Hz | 3.3 | 3.5 | 3.3 | 3.5 | 3.3 | 3.3 |
| | | 1 KHz | 3.2 | 3.5 | 3.3 | 3.5 | 3.3 | 3.2 |
| | | 100 KHz | 3.2 | 3.4 | 3.2 | 3.5 | 3.2 | 3.1 |
| | water resistance (%) | | 0.33 | 0.35 | 0.33 | 0.36 | 0.34 | 0.31 |

Experiment 12

100 Parts (by weight, hereinafter the same) of Epikote 828 [trade name of 2,2-bis(4-hydroxyphenyl)propane glycidyl ether; epoxy equivalency: 189; made by Shell International Chemicals Corp.], 120 parts of the liquid maleinized allo-ocimene obtained in Example 15, and 1 part of an accelerator of benzyldimethylamine were uniformly mixed at a normal temperature, and defoamed under reduced pressure (not higher than 2 mm Hg) to prepare an epoxy resin composition. This composition had a viscosity of about 23 poises at 25° C., and casting of the composition was conducted with extreme ease.

When this resin composition was pre-cured for 3 hours at 80° C. and post-cured for 6 hours at 120° C., there was obtained a tough cured resin as shown in Table 16.

Experiment 13

In the same manner as in Experiment 12 except for using the liquid product obtained in Example 69 in place of the liquid maleinized allo-ocimene, there was obtained a cured product. Physical properties of this cured product are shown in Table 16.

TABLE 16

| | | Experiment 12 | Experiment 13 |
|---|---|---|---|
| Formulation (parts by weight) | Epikote 828 | 100 | 100 |
| | Hardener | 120 | 120 |
| | Benzyldimethylamine | 1 | 1 |
| Physical Properties of Cured Product | thermal deformation temperature (°C.) | 110 | 115 |
| | bending strength (kg/cm$^2$) | 13.5 | 14.0 |
| | bending modulus of electricity (kg/cm$^2$) | 300 | 320 |
| | thermal shock resistance | 1 | 1 |
| | dielectric constant ($\epsilon$) | | |
| | 60 Hz | 3.1 | 3.0 |
| | 1 KHz | 3.0 | 3.0 |
| | 100 KHz | 3.0 | 3.0 |

What is claimed is:

1. A process for liquefying a normally solid Diels-Alder reaction product between maleic anhydride and decatriene, which comprises heat-treating at 60° to 250° C. the reaction product in the presence of a compound selected from the following groups (a) to (e):
   (a) alkali metal salts;
   (b) nitrogen atom-containing organic compounds;
   (c) phosphorus atom-containing compounds selected from phosphines and quaternary phosphonium salts;
   (d) thiocyanates; and
   (e) solid basic compounds (except the alkali metal salts belonging to group (a) described above, wherein the amount of said compound selected from groups (a) to (e) is 0.005 to 3.0 parts by weight per 100 parts by weight of said solid Diehls-Alder reaction product between maleic anhydride and decatriene.

2. A process for liquefying the reaction product as in claim 1, wherein said decatriene is allo-ocimene.

3. A process for liquefying the reaction product as in claim 1, wherein said decatriene is 2,6-dimethyl-3,6-octatriene.

4. A process for liquefying the reaction product as in claim 1, wherein said heat treatment is conducted in the presence of an alkali metal salt.

5. A process for liquefying the reaction product as in claim 4, wherein said alkali metal salt is selected from lithium bromide and sodium iodide.

6. A process for liquefying the reaction product as in claim 1, wherein said compound selected from the groups (a) to (e) functions as an isomerization catalyst.

7. A process for liquefying the reaction product as in claim 1, wherein the heat-treating temperature is from 100° to 220° C.

8. A process for liquefying the reaction product as in claim 1, wherein the heat-treating time is from 10 minutes to 10 hours.

9. A process for liquefying the reaction product as in claim 1, wherein the heat-treating time is from 0.5 to 3 hours.

10. A process for liquefying the reaction product as in claim 1, wherein a further heat-treating is conducted in the presence of an acidic catalyst or a noble metal catalyst to improve liquid stability, said further heat-treating being at from 50° to 250° C. for from 5 minutes to 8 hours in the presence of 0.001 part by weight or more 100 parts by weight of said reaction product between maleic anhydride and decatriene with respect to the noble metal catalyst and from 1 to 15 parts by weight with respect to ion exchange resins, silica and alumina as an acidic catalyst and 0.1 to 5 parts by weight with respect to other acidic catalysts.

11. A process for liquefying the reaction product as in claim 1, wherein said heat treatment is conducted in the presence of said nitrogen atom-containing organic compounds.

12. A process for liquefying the reaction product as in claim 1, wherein said heat treatment is conducted in the presence of said phosphorous atom-containing compounds.

13. A process for liquefying the reaction product as in claim 1, wherein said heat treatment is conducted in the presence of said thiocyanates.

14. A process for liquefying the reaction product as in claim 1, wherein said heat treatment is conducted in the presence of said solid basic compound.

* * * * *